United States Patent [19]

Wuest et al.

[11] Patent Number: 5,510,482
[45] Date of Patent: Apr. 23, 1996

[54] PROCESS FOR BLEACHING DISCOLORED SURFACE-ACTIVE ALKYL GLYCOSIDES AND FOR WORKING UP THE BLEACHED MATERIAL

[75] Inventors: Willi Wuest, Ratingen; Rainer Eskuchen, Duesseldorf; Paul Schulz, Wuppertal; Volker Bauer, Duesseldorf; Franz-Josef Carduck, Haan; Herbert Esser, Troisdorf; Christiane Zeise, Korschenbroich; Manfred Weuthen, Solingen; Josef Penninger, Hilden, all of Germany

[73] Assignee: Henkel Kommanditgesellschaft auf Aktien, Duesseldorf, Germany

[21] Appl. No.: 324,318

[22] Filed: Oct. 17, 1994

Related U.S. Application Data

[63] Continuation of Ser. No. 960,427, Feb. 11, 1993, abandoned.

[30] Foreign Application Priority Data

Jun. 15, 1990 [DE] Germany ............ 40 19 175.3

[51] Int. Cl.$^6$ .................... C07H 1/06; C07H 15/04
[52] U.S. Cl. .................... 536/127; 536/124; 536/18.6
[58] Field of Search .................... 536/127, 124, 536/18.6, 18.5

[56] References Cited

U.S. PATENT DOCUMENTS

| | | | |
|---|---|---|---|
| 3,450,690 | 6/1969 | Gibbons et al. | 536/18.5 |
| 3,839,318 | 10/1974 | Mansfield | 536/18.6 |
| 4,223,129 | 9/1980 | Roth et al. | 536/18.6 |
| 4,510,306 | 4/1985 | Langdon | 536/127 |
| 4,557,729 | 12/1985 | McDaniel et al. | 536/18.5 |
| 4,847,368 | 7/1986 | Lueders et al. | 536/18.6 |
| 4,959,468 | 9/1990 | Ravi et al. | 536/18.6 |
| 4,963,158 | 10/1990 | Beaujean et al. | 252/90 |

FOREIGN PATENT DOCUMENTS

| | | |
|---|---|---|
| 0102558 | 3/1984 | European Pat. Off. . |
| 165721 | 5/1985 | European Pat. Off. . |
| 306652 | 7/1988 | European Pat. Off. . |
| 365831 | 9/1989 | European Pat. Off. . |
| 9003977 | 4/1990 | WIPO . |
| 9003216 | 5/1990 | WIPO . |
| 9102046 | 2/1991 | WIPO . |

Primary Examiner—Douglas W. Robinson
Assistant Examiner—Everett White
Attorney, Agent, or Firm—Wayne C. Jaeschke; John E. Drach; Henry E. Millson, Jr.

[57] ABSTRACT

The crude reaction products from the synthesis of alkyl glycosides are bleached by kneading the material substantially freed from the excess fatty alcohol and containing at most limited quantities of water with an oxidizing agent at such elevated temperatures that the reaction mixture lends itself to plastic processing. Temperatures of from about 50° to 150° C. are particularly suitable, although it is best to apply temperatures in the range from about 80° to 100° C. using aqueous hydrogen peroxide as the oxidizing agent. Bleaching is carried out under basic conditions, optionally by addition of an alkaline compound, such as for example 50% sodium hydroxide solution. The bleached product accumulates in the form of a solid. It is preferably mixed with typical compatible solids, more particularly typical constituents of detergents and cleaning preparations, to form a solid and preferably free-flowing alkyl glycoside compound.

19 Claims, No Drawings

PROCESS FOR BLEACHING DISCOLORED SURFACE-ACTIVE ALKYL GLYCOSIDES AND FOR WORKING UP THE BLEACHED MATERIAL

This application is a continuation of application Ser. No. 07/960,427 filed on Feb. 11, 1993, now abandoned.

BACKGROUND OF THE INVENTION

Surface-active alkyl glycosides are the known reaction products of sugars and relatively long-chain alcohols, more particularly aliphatic primary alcohols preferably containing 8 to 22 carbon atoms. The sugar component may be selected from any of the aldoses or even ketoses in the broad sense (hereinafter referred to as glycoses), including for example glucose, fructose, mannose, galactose, talose, gulose, allose, altrose, idose, arabinose, xylose, lyxose and ribose. Aldoses are preferably used in the synthesis of alkyl glycosides by virtue of their increased reactivity. Among the aldoses, glucose is particularly suitable because it is readily obtainable and available in industrial quantities. Accordingly, among the compounds in question, those preferably used in practice are surface-active alkyl glucosides. Their alkyl radical is preferably derived from primary aliphatic alcohols of synthetic origin, but especially from those of natural origin. The fatty alcohol radical is attached by an acetal bond to a mononuclear glucose residue and/or to oligo or polysaccharide residues. For the purposes of the invention, these names are regarded as synonymous with one another.

Surface-active alkyl glycosides are obtained either by the so-called direct synthesis method from relatively long-chain alcohols or alcohol mixtures and sugars or sugar-yielding polymer compounds, particularly starch, or by transacetalization of alkyl glycoside compounds obtained in a preliminary step with a comparatively short-chain alcohol radical attached by an acetal bond. The acetalization or transacetalization is carried out in the presence of a considerable excess of the relatively long-chain alcohols in the presence of acidic acetalization catalysts. To obtain the alkyl glycosides in pure form from the crude reaction products, the acidic catalysts first have to be neutralized and the excess of the long-chain alcohols removed. The alcohols are generally removed by thin-layer evaporation at considerably elevated temperature, sump temperatures of 160° to 210° C. being quite normal. The reaction product accumulating generally solidifies at temperatures above 100° C. and forms dark-colored masses which are solid at room temperature.

These initial reaction products, which are deep dark brown in color, are unsuitable for the practical application of the alkyl glycosides, for example as highly effective surfactant components for domestic and institutional detergents and cleaning preparations. Accordingly, a regular part of the synthesis process is a post-synthesis step in which the crude reaction products initially obtained are bleached. There are many prior publications relating to the production and recovery of pure surface-active alkyl glycosides in the form of light-colored reaction products, cf. U.S. Pat. Nos. 3,454,690 and 3,839,318, European patent applications 102 558 and 165 721 and, in particular, International patent application WO90/03977 ("A process for the direct production of alkyl glycosides"). According to these documents, oxidative bleaching of the crude alkyl glycoside compounds initially accumulating as dark-colored reaction products is generally necessary as an essential step of the process as a whole. Hydrogen peroxide in particular and/or compounds yielding hydrogen peroxide have proved to be optimal bleaches.

More particularly, the bleaching step is carried out as follows:

On completion of acetalization or transacetalization, the hot reaction mixture is slightly cooled, for example to around 90° C., after which organic or inorganic basic alkali metal, alkaline earth metal and/or aluminium compounds are added in such quantities that not only is the acidic catalyst neutralized, a pH value of at least about 8 and preferably in the range from about 8 to 10 is established. The excess alcohol is then distilled off in a vacuum, more particularly a high vacuum, in standard distillation apparatus, for example in a thin-layer evaporator or in a falling-film evaporator, to residual free alcohol contents of less than about 5% by weight, based on the reaction product as a whole. The distillation residue is then cooled to around 105° C. and an approximately 30 to 60% paste is produced by addition of water. It is this paste-form preparation of the alkyl glycoside compounds which is subjected to bleaching. To this end, an active oxygen compound, preferably hydrogen peroxide, is normally added to the aqueous paste-form preparation with stirring over a period of about 0.1 to 5 hours at approximately 80° C., the pH value being kept in the range from about 8 to 10 during this bleaching step, optionally by addition of alkali, preferably sodium hydroxide. The production process hitherto carried out in practice is characterized by this oxidative bleaching of the aqueous alkyl glycoside paste, in which the water containing partly dissolved alkyl glycosides forms the continuous phase while the insoluble alkyl glycoside excess forms the disperse phase. This known measure leads to light-colored, stable products. However, recovery of the alkyl glycosides as a dry solid or as a constituent of dry active-substance mixtures always requires the removal of appreciable quantities of water, which adds considerably to the cost of the process.

DESCRIPTION OF THE INVENTION

The problem addressed by the present invention was to find a way in which light-colored, more particularly white, dry alkyl glycoside compounds could be produced with inclusion of a bleaching step, but without intermediate formation of the aqueous paste form.

The present invention relates to a process for bleaching discolored surface-active alkyl glycosides, more particularly crude reaction products from the synthesis of alkyl glycosides, by oxidative bleaching in the basic range and working up of the bleached material, characterized in that the material substantially freed from the excess fatty alcohol and containing at most limited quantities of water is kneaded with the oxidizing agent at such elevated temperatures that the reaction mixture lends itself to plastic: processing. The process according to the invention is carried out in particular at a temperature in the range from about 50° to 150° C. and preferably at a temperature in the range from about 80° to 100° C.

The crux of the teaching according to the invention is the discovery that effective oxidative bleaching of the dark-colored alkyl glycoside compounds does not require the preparation of an aqueous paste with a continuous aqueous phase and a very finely divided, solid, disperse alkyl glycoside, which has hitherto been regarded as necessary, instead the alkyl glycoside itself, as the homogeneous phase of the material to be bleached, can also be effectively subjected to the bleaching treatment under selected reaction conditions.

Crucial to this process is the property which the alkyl glycosides have of softening plastically at elevated temperatures to form highly viscous masses, even before they are melted to form the flowable phase, to such an extent that the chemical reaction in the form of the desired bleaching can be carried out effectively throughout the entire plastically softened material. It may be appropriate to raise the product temperature to such an extent that plastic, i.e. highly viscous, masses are formed, substantially corresponding in their behavior to a bread dough of the type processed in bakeries. The oxidizing agent and the alkalizing agent may then be mixed in the small quantities required into the plasticized mass and homogeneously distributed therein so that adjustment of the desired pH value of at least about 8 and, more particularly, in the range from about 8 to 10 and also full reaction of the oxidizing agent with the impurities responsible for the discoloration are both guaranteed.

Basically, suitable oxidizing agents are any of the known representatives of this type, i.e. in particular hydrogen peroxide, peroxidic compounds, for example of the perborate and percarboxylic acid type, if desired even in conjunction with bleach activators of the type known, for example, from laundry detergents. It is particularly easy to use hydrogen peroxide, which ultimately yields water in addition to the bleached product as a secondary product of the reaction, so that the preferred embodiment of the process according to the invention is characterized by the use of hydrogen peroxide mildly alkalized by the use of an alkalizing agent.

The oxidizing agent, i.e. in particular the hydrogen peroxide, and also the alkalizing agent required to establish the desired pH value may be used together with small quantities of liquid phase. The preferred solvent here is water, so that typical aqueous peroxide solutions or aqueous base solutions are the additives in the preferred embodiment of the process according to the invention. Aqueous hydrogen peroxide having peroxide concentrations of 10 to 60% by weight and aqueous alkali hydroxide solutions, for example aqueous sodium hydroxide having a concentration in the same range, can be particularly suitable auxiliaries for the purposes of the process according to the invention. The aqueous solution or dispersion of the oxidizing agent is preferably used in a quantity below 10% by weight and more particularly in a quantity of 3 to 8% by weight. In the preferred embodiment, the oxidizing agent and the aqueous base are used in such limited quantities that the limited, water content in the plasticized reaction mixture makes up no more than at most about 20% by weight and is preferably in the range from 5 to 10% by weight. These reactants or reaction auxiliaries are incorporated in the plastically softened alkyl glycoside in particular by intensive kneading of the plasticized reaction mixture with permanent surface renewal. At the elevated temperatures of around 100° C. mentioned above, reaction times of up to about 15 minutes are entirely sufficient for lightening or even for complete decoloration of the crude alkyl glycoside. A treatment time under the process conditions according to the invention of up to about 10 minutes and, in particular, a kneading time of from about 3 to 5 minutes are preferred elements in the context of the invention. The end products of the process according to the invention are suitable for applications requiring bleached alkyl glycosides in bleached anhydrous form. Another advantage is that the end products of the process contain hardly any residual peroxy compounds.

The plasticized alkyl glycoside compounds and the above-mentioned auxiliaries, which are used in small quantities in accordance with the invention, may be processed either in batches or continuously. Batch processing is possible, for example, in intensive kneaders of the type known, for example, for the kneading of bread doughs. In the industrial production and working up of alkyl glycosides, however, bleaching in the context of the proposal according to the invention is intended as a continuous process step and is incorporated in the continuous production process. This is readily possible by using mixing and kneading extruders which are used in accordance with the invention as the mixing and bleaching zone. It may be appropriate in this regard initially to plasticize the alkyl glycoside starting material in a preliminary stage carried out in the absence of oxidizing and alkalizing agents or to incorporate only the alkalizing agent in this preliminary step. The aqueous hydrogen peroxide is then introduced in a subsequent process step where multiple-step introduction in successive sections or zones of the extruder is again possible. Gaseous decomposition products can be removed from the reaction mass in a degassing zone provided in the rear part of the extruder. The bleached alkyl glycoside product containing at most small quantities of water emerges at the extruder exit. It can be worked up in various ways, as will be described hereinafter.

The preferred starting materials for the bleaching process according to the invention are the crude reaction products from the production of alkyl glycosides in the form in which they accumulate in the process normally used after removal of the excess fatty alcohol. The crude reaction products in question are characterized by the data disclosed in the above-cited International patent application WO90/03977. The industrial production of a $C_{12/14}$ alkyl glucoside is described in Example 3 of this document, according to which the crude alkyl glucoside accumulates after removal of the excess fatty alcohol in the form of a solidified melt containing approximately 63% by weight fatty alkyl monoglucoside, 15% by weight fatty alkyl diglucoside, 6% by weight fatty alkyl triglucoside, 3% by weight alkyl tetraglucoside, 6% by weight polyglucose and 2 to 4% by weight residual fatty alcohol. According to the disclosure of this document, approximately 88 kg water at room temperature are added in batches (90 kg) to this product in molten form at 150° C. in a pressure vessel, resulting in the formation of an approximately 50% paste. By addition of very limited quantities of a 35% $H_2O_2$ solution (1.3 kg) and 0.9 kg of a 50% NaOH solution, the desired bleaching effect is obtained after stirring for 3 hours at 90° C.

The present invention dispenses with this step of preparing the aqueous paste. Instead, the process according to the invention is directly applied to the plastically softened material, as described in detail in the following Examples.

The bleached reaction product leaving the extruder used for bleaching may be worked up in virtually any form. Three characteristic possibilities are mentioned below:

The alkyl glycoside leaving the extruder may be brought as such into a certain form of a solid by cooling and size-reduction; for example, it is worked up into granules.

On the other hand, the alkyl glycoside may be worked up for subsequent mixing with aqueous liquids to form an aqueous paste having any solids contents, for example in the range from about 40 to 60% by weight.

In the third embodiment, which will be particularly significant for many applications, the purified alkyl glycoside may be combined with solids, more particularly by intensive mixing. The mixtures formed may then be subjected, for example, to granulation.

The last of the three above-mentioned possibilities covers numerous embodiments of the procedure according to the invention. The substances added to the alkyl glycosides are auxiliaries in the broadest sense which have an intrinsic effect in the subsequent application envisaged for the alkyl glycosides or which may be regarded merely as auxiliaries for the improved or simplified industrial utilization of the alkyl glycosides. Examples of possible additives can be found in applicants' earlier International patent application WO91/02046 ("Powder-form preparations of surface-active alkyl glycosides") which describes powder-form preparations of surface-active alkyl glycosides in admixture with inert inorganic supports, the alkyl glycosides sides making up from 5 to 65% by weight and the inert supports the remainder of the mixture. The inorganic supports mentioned include, for example, chalk, silicas, dicalcium phosphate, calcium pyrophosphate, water-insoluble sodium metaphosphate, aluminium oxide, aluminium oxide hydrate, sodium chloride, sodium sulfate or mixtures of these substances. Mixtures of this type are intended in particular for use in the cosmetics field, for example in oral and dental hygiene preparations.

Other interesting mixture components fall within the scope of the invention where the alkyl glycosides are intended for other characteristic applications, more particularly domestic and institutional detergents and/or cleaning preparations. In this case, the alkyl glycosides may be mixed with typical, preferably fine-particle ingredients of detergents and cleaning preparations and worked up with them into granules. Alkalizing agents, such as soda, or builder components, such as alkali polyphosphates and, in particular, detergent-quality zeolite NaA, are mentioned purely by way of example. However, mixtures of the alkyl glycosides with other surfactant components may be considered even at this stage. In this case, the alkyl glycoside may be incorporated in virtually any quantities in the multicomponent mixture formed, so that—numerically—quantities of 5 to 95% by weight alkyl glycoside may be used to quantities of 95 to 5% by weight of the mixture component (s).

Interesting possibilities for preparing the multicomponent mixtures containing alkyl glycoside are available in this particular regard, as mentioned by way of example in the following:

Where solids capable of immobilizing water present in the multicomponent mixture by binding water with internal formation of water of crystallization are at least partly used as components of the mixture together with the bleached alkyl glycosides, it is possible to prepare multicomponent granules which are substantially free from the water introduced during bleaching or may even be completely dry. A classic example of this is mixing with calcined soda or sodium sulfate in anhydrous or substantially anhydrous form.

On the other hand, rapid disintegration of these intermediately formed multicomponent granules can be promoted by the use of auxiliaries, more particularly so-called disintegrating agents and/or cold-soluble auxiliaries. Typical examples of disintegrating agents are inorganic components, for example of the swellable layer silicate type, such as bentonites, or corresponding organic materials of natural origin or derivatives thereof, more particularly starch, cellulose and/or derivatives thereof, such as CMC, MC, alginate compounds and the like. Cold-soluble auxiliaries are readily soluble salts, for example sodium acetate, urea and also percarbonates and any other corresponding cold-soluble auxiliaries with or without an intrinsic effect for the subsequent application envisaged, for example in detergents and cleaning preparations. Purely synthetic auxiliaries, of the type known for example in the form of the alkali metal salts of polyacrylates or polymethacrylates of comparatively low molecular weight, can also be of particular significance in this regard. Polymer components of this type having average molecular weights of from about 1,000 to 5,000 and more particularly in the range from about 1,000 to 3,000 are distinguished by a strong dispersing effect, even when used in small quantities, so that additions of less than 10% by weight and preferably less than 1% by weight can substantially accelerate primary disintegration of the granules.

EXAMPLES

Example 1

Immediately after removal of the excess fatty alcohol to a residual content of 2 to 3% by weight, a quantity of 1 kg alkyl glucoside ($C_{12/14}$ alkyl, degree of oligomerization 1.4) was removed from a thin-layer evaporator and introduced into a heatable laboratory kneader (temperature of the melt approx. 120° C.). After cooling to approximately 100° C., 40 g of a 50% sodium hydroxide solution (2% by weight sodium hydroxide, based on the alkyl glycoside) were added with mixing. A plastic mass having a temperature of 80° C. was thus obtained. 67 g of a 30% aqueous $H_2O_2$ solution were then added over a period of 30 minutes with continuous kneading, followed by thorough mixing for 15 minutes at 80° C. The plastic mass was then discharged and, after cooling, 1 kg sodium carbonate powder was added with size-reduction, after which the material was homogenized to form white free-flowing granules.

Example 2

5 kg of the alkyl glucoside of Example 1 were mixed with the aqueous sodium hydroxide and hydrogen peroxide solutions at 90° C. in a heatable laboratory kneader. 100 g of a 50% sodium hydroxide solution was added first and, after a temperature of around 90° C. had been established, 168 g of a 30% $H_2O_2$ solution were introduced over a period of 30 minutes. After-mixing time at 90° C.: 15 minutes. A pale yellow reaction product was obtained and, after size-reduction and homogenization, was mixed with 10 kg zeolite A to form white free-flowing granules.

Where the process according to the invention is carried out in an extruder as a continuous kneading unit, the kneading times can be shortened to less than 15 minutes compared with those in a laboratory kneader.

Example 3

In a laboratory kneader, 1.5 g NaOH (50%) and then 2.5 g $H_2O_2$ (30%) were added to 150 g of a $C_8$ alkyl polyglucoside (degree of oligomerization 1.7) at a temperature of 90° C. 30 Minutes later, the temperature was increased to 110° C. and kept at that level for 2 hours. During the last 30 minutes, vacuum (approx. 1 to 10 mbar) was applied to remove the water. 75 g $Na_2SO_4$ (anhydrous) were then added at approximately 100° C. After thorough mixing, the mixture obtained was ground at room temperature (laboratory mixer). The color quality was determined as a Klett value (3% in isopropanol/water) of 11. The peroxide value was below 1.

Example 4

In a laboratory kneader, 3.0 g NaOH (50%) and then 5.0 g $H_2O_2$ (30%) were added to 150 g of a $C_{12/14}$ alkyl polyglucoside (degree of oligomerization 1.4) at an internal temperature of 90° C. 30 Minutes later, the temperature was increased to 110° C. and was kept at that level for 2 hours. During the last 30 minutes, vacuum (approx. 1–10 mbar)

was applied to remove the water. The product is ground at room temperature (laboratory mixer). Klett value (5% in isopropanol/water): 17. Peroxide value: below 1.

Example 5

150 g of a $C_6$ alkyl polyglucoside (degree of oligomerization 1.4) were treated as in Example 4 with 1.5 g NaOH (50%) and 2.5 g $H_2O_2$ (30%). A very light-colored powder having a Klett value (5% in toluene) of 25 was thus obtained. Peroxide value: below 1.

What is claimed is:

1. A process for bleaching a discolored surface active alkyl glycoside comprising the steps of:
    (1) providing an alkyl glycoside reaction product having less than about 5.0% by weight of residual fatty alcohol;
    (2) forming a plasticized mass having less than about 10% by weight of water and having a pH of from about 8 to about 10, at a temperature in the range of from about 50° C. to about 150° C., by adding an aqueous solution of an oxidizing agent and an aqueous alkaline solution to said alkyl glycoside reaction product; and
    (3) kneading said plasticized mass at a temperature in the range of from about 50° C. to about 150° C. to form a bleached surface active alkyl glycoside product in the form of a plastic mass.

2. The process of claim 1 wherein said temperature range in steps (2) and (3) is from about 80° C. to about 100° C.

3. The process of claim 1 wherein step (3) is carried out for less than about 15 minutes.

4. The process of claim 1 further comprising adding water to said bleached surface active alkyl glycoside product to form a paste.

5. The process of claim 1 further comprising the step of forming a granulated product from said bleached surface active alkyl glycoside product by cooling the plastic mass from step (3) and size-reducing the resulting solid.

6. The process of claim 1 wherein said process is carried out in an extruder.

7. The process of claim 1 wherein step (3) is carried out for from about 3 to about 5 minutes.

8. The process of claim 1 wherein following step (3) the plastic mass is intensively mixed with solid auxiliary components.

9. The process of claim 8 wherein the mixture containing the solid auxiliary components is size reduced to produce granules thereof.

10. The process of claim 1 wherein in step (2) the amount of water present in said plasticized mass is not more than about 6%.

11. The process of claim 10 wherein the amount of water is not more than about 5%.

12. The process of claim 10 wherein the amount of water is not more than about 3.2%.

13. A continuous process for bleaching a discolored surface active alkyl glycoside comprising the steps of:
    (A) in a first reaction zone plasticizing an alkyl glycoside reaction product having less than about 5.0% by weight of residual fatty alcohol at a temperature in the range of from about 50° C. to about 150° C.;
    (B) in a second reaction zone forming a plasticized mass having less than about 10% by weight of water and having a pH of from about 8 to about 10, at a temperature in the range of from about 50° C. to about 150° C., by adding an aqueous solution of an oxidizing agent and an aqueous alkaline solution to said plasticized alkyl glycoside reaction product;
    (C) kneading said plasticized mass at a temperature in the range of from about 50° C. to about 150° C. to form a bleached surface active alkyl glycoside product in the form of a plastic mass, while continuously removing gaseous decomposition products therefrom; and
    (D) continuously removing said bleached surface active alkyl glycoside product from step (C).

14. The continuous process of claim 13 wherein steps B) and C) are carried out in an extruder.

15. The process of claim 13 wherein in step (B) the amount of water present in said plasticized mass is not more than about 6%.

16. The process of claim 15 wherein the amount of water is not more than about 5%.

17. The process of claim 15 wherein the amount of water is not more than about 3.2%.

18. A continuous process for bleaching a discolored surface active alkyl glycoside comprising the steps of:
    (A) in a first reaction zone mixing together an aqueous alkaline solution and an alkyl glycoside reaction product having less than about 5.0% by weight of residual fatty alcohol, and plasticizing the alkyl glycoside reaction product at a temperature in the range of from about 50° C. to about 150° C.;
    (B) in a second reaction zone forming a plasticized mass having less than about 10% by weight of water and having a pH of from about 8 to about 10, at a temperature in the range of from about 50° C. to about 150° C., by adding an aqueous solution of an oxidizing agent to said plasticized alkyl glycoside reaction product;
    (C) kneading said plasticized mass at a temperature In the range of from about 50° C. to about 150° C. to form a bleached surface active alkyl glycoside product in the form of a plastic mass, while continuously removing gaseous decomposition products therefrom; and
    (D) continuously removing said bleached surface active alkyl glycoside product from step (C).

19. The continuous process of claim 18 wherein steps B) and C) are carried out in an extruder.

* * * * *